United States Patent [19]
Tirosh et al.

[11] Patent Number: 6,165,501
[45] Date of Patent: *Dec. 26, 2000

[54] RADIATION-PROTECTIVE PHOSPHOLIPID AND METHOD

[75] Inventors: Oren Tirosh, Holon; Ron Kohen, Jerusalem; Jehoshua Katzhendler, Jerusalem; Yechezkel Barenholz, Jerusalem, all of Israel

[73] Assignee: Yissum Research Development Company of the Hebrew University of Jerusalem

[ * ] Notice: This patent is subject to a terminal disclaimer.

[21] Appl. No.: 09/167,403

[22] Filed: Oct. 6, 1998

Related U.S. Application Data

[63] Continuation-in-part of application No. 08/570,440, Dec. 11, 1995, Pat. No. 5,817,856.

[51] Int. Cl.⁷ .................................................. A61K 9/127
[52] U.S. Cl. ........................... 424/450; 558/169; 558/186
[58] Field of Search ............................ 424/450; 558/169, 558/186; 514/78

[56] References Cited

U.S. PATENT DOCUMENTS

| | | |
|---|---|---|
| 4,426,330 | 1/1984 | Sears . |
| 4,534,899 | 8/1985 | Sears . |
| 4,772,471 | 9/1988 | Vanlerberghe et al. . |
| 5,013,556 | 5/1991 | Woodle ................................... 424/480 |
| 5,190,915 | 3/1993 | Behan et al. . |
| 5,252,555 | 10/1993 | Dartnell et al. . |
| 5,817,856 | 10/1998 | Tivosh .................................... 558/169 |

FOREIGN PATENT DOCUMENTS

| | | |
|---|---|---|
| 0 118 316 | 9/1984 | European Pat. Off. . |
| 0 370 491 | 5/1990 | European Pat. Off. . |
| 7316040 | 12/1995 | Japan . |
| WO 91/05545 | 5/1991 | WIPO . |

OTHER PUBLICATIONS

Allen, T.M., "Stealth Liposomes: Five Years On," *J. Liposome Research* 2 (3) :289–305 (1992).

Brezesinski, G., et al., "Influence of Ether Linkages on the Structure of Double–Chain Phospholipid Monolayers," *Chemistry and Physics of Lipids* 76:145–157 (1995).

Hing, F.S., et al., "Structure and Interactions of Ether–and Ester–Linked Phosphatidylethanolamines," *Biochemistry* 30(37):9007–9015 (1991).

Hristova, K., and Needham, D., "Phase Behavior of a Lipid/Polymer–Lipid Mixture in Aqueous Medium," *Macromolecules* 28:991–1002 (1995).

Kim, J.T., et al., "Gel Phase Polymorphism in Ether–Linked Dihexadecylphosphatidylcholine Bilayers, " *Biochemistry* 26:6592–6598 (1987).

Kim, J.T., et al., "Bilayer Interactions of Ether–and Ester–Linked Phospholipids: Dihexadecyl–and Dipalmitoylphosphatidylcholines, " *Biochemistry* 26:6599–6603 (1987).

Lindh, I., and Stawi_ski, J., "A General Method for the Synthesis of Glycerophophospholipids and Their Analogues via H–Phosphonate Intermediates," *J. Org. Chem.* 54:1338–1342.

Ukawa, K., et al., "Synthesis and Antitumor Activity of New Amphiphilic Alkylglcerolipids Substituted with a Polar Head Group, 2–(2–Trimethylammonioethoxy) ethyl or a Congeneric Oligo (ethyleneoxy) ethyl Group," *Chem. Pharm. Bull.* (12) :3277–3285 (1989.

Wheeler, J.J., et al., "Polyethylene Glycol Modified Phospholipids Stabilize Emulsions Prepared from Triacylglycerol," *J. Pharmaceutical Sciences* 83(11) :1558–1564 (1994).

*Primary Examiner*—Gollamudi S. Kishore
*Attorney, Agent, or Firm*—LeeAnn Gorthey

[57] ABSTRACT

Ether-linked phospholipids, derivatized at the polar head group with polyethylene glycol chains having molecular weights greater than 2,000 daltons, are disclosed. Lipid bilayers containing these phospholipids show high oxidative stability. Also disclosed is the use of PEG-derivatized ether-linked lipids in moisturizing and radiation-protective cosmetic compositions.

10 Claims, 7 Drawing Sheets

RADIATION-PROTECTIVE PHOSPHOLIPID AND METHOD

This application is a CIP of Ser. No. 08/570,440 filed Dec. 11, 1995, now U.S. Pat. No. 5,817,856.

FIELD OF THE INVENTION

This application claims priority to U.S. application Ser. No. 08/570,440, filed Dec. 11, 1995, which is hereby incorporated by reference in its entirety.

The present invention relates to radiation-protective ether-linked phospholipids, to cosmetic compositions containing the phospholipids, and to methods of protecting the skin and lipid-containing compositions from oxidative damage.

References

Barenholz, Y., and Amselem, S., in *Liposome Technology*, 2nd edition, Gregoriadis, G., ed., CRC Press, Boca Raton, 1993, pp. 501–525.

Barenholz, Y. et al., *Biochemistry* 22:3497–3501 (1983).

Haran, G. et al., *Biochim. Biophys. Acta.* 1151:201–215 (1993).

Johnson, R. M. and Siddiqi, I. W., in *The Determination of Organic Peroxides*, Pergamon Press, 1966, pp. 50–52.

Kates, M., Chan, T. H., and Stanacev, N. Z., *Biochemistry* 2:394–396 (1963).

Lindh, I., and Stawinski, J., *J. Org. Chem.* 54:1338–1342 (1989).

Miyazaki, H. et al., U.S. Pat. No. 5,428,030 (June 1995).

Nishida, T. et al., U.S. Pat. No. 5,433,944 (July 1995).

Sears, B. D., U.S. Pat. No. 4,426,330 (January 1984).

Sears, B. D., U.S. Pat. No. 4,534,899 (August 1985).

Szoka, F., Jr., et al., U.S. Pat. No. 4,235,871 (November 1980).

Szoka, F., Jr., et al., *Ann. Re. Biophys. Bioeng.* 9:467 (1980).

Uster, P. S. et al., *Biochemistry* 24(1):1–8 (1985).

Woodle, M. C. et al., U.S. Pat. No. 5,013,556 (May 1991).

BACKGROUND OF THE INVENTION

Cosmetic formulations containing lipids are well known. Lipids can function to produce the desired consistency and viscosity in a formulation and, more importantly, to help replenish lipids in the skin.

Since most lipids commonly used in cosmetic formulations contain unsaturated chains, such formulations are susceptible to oxidation. Oxidative damage can lead to loss of alkyl chains, which results in loss of fluidity and lipophilic properties, e.g., the ability to replenish lipids in the skin and thus impart suppleness and youthful appearance. Oxidation can also lead to discoloration and development of unpleasant odors. Oxidative damage can be attributed, in particular, to radiation-induced free radical reactions.

In addition to minimizing oxidation, it is desirable to enhance the moisturizing properties of cosmetic formulations; i.e., the amount of moisture that can be retained by the skin when the formulation is applied. Increased moisturizing effectiveness is also important in topical therapeutic lipid formulations, such as are used in treating dry eyes.

Finally, it is desirable that the lipids themselves are stable; e.g., that they not be readily oxidized or hydrolyzed.

SUMMARY OF THE INVENTION

The present invention includes, in one aspect, a dialkyl ether-linked phospholipid having a phosphorus containing polar head group. The polar head group is derivatized with a polyethylene glycol (PEG) chain which has a molecular weight of at least 2,000 daltons, and preferably at least 10,000 daltons. In one embodiment, the PEG chain has a molecular weight between about 2,000 and 125,000 daltons. In a preferred embodiment, the phospholipid has ether-linked $C_{16}$ to $C_{24}$ alkyl or alkenyl chains. The alkenyl chains are preferably monoalkenyl.

The phospholipid may have a negatively charged polar head group, such as a phosphate group. The head group may alternatively be neutrally charged, e.g., a lower alkyl phosphate ester, or positively charged, e.g., a lower alkyl phosphate ester whose alkyl component is terminated with a charged amine.

In another aspect, the invention includes a cosmetic composition, comprising liposomal or micellar lipid particles suspended in an aqueous medium. The particles contain 1–25 mole percent of an ether-linked PEG-derivatized phospholipid, as described above, and the remainder vesicle-forming lipids, in the case of liposome particles. The micellar particles contain greater than 25 mole percent of an ether-linked PEG-derivatized phospholipid, and the remainder vesicle-forming lipids. In a preferred embodiment, the dialkyl ether-linked phospholipid of the composition is substituted with a PEG chain, as described above.

In one embodiment of the composition, which combines high viscosity with low lipid concentration, the ionic strength of the aqueous medium of the composition is less than about 10 mM salt, and the total lipid concentration is between about 5 mM and about 200 mM, and preferably between about 50 mM and about 150 mM.

The cosmetic composition additionally may include one or more cosmetically useful components, such as antioxidants, preservatives, thickeners, humectants, dyes, fragrances, emollients, conditioners, collagen, elastin, vitamins, enzymes, antibiotics, bactericides, or UV-absorbing compounds. In a preferred embodiment, the cosmetic composition includes a UV-absorbing compound and is suitable for use as a sun-protection composition.

In another embodiment, the cosmetic lipid composition includes one or more of the following components: isotonicating agents, preservatives, buffering agents, viscosity-increasing agents, solubilizing agents, and stabilizers, and has a pH between about 5.0 and about 8.0. Such a composition is suitable for use in eye drops.

The invention provides, in another aspect, a method of protecting the skin against radiation damage, by applying to the skin a cosmetic composition comprising liposomal or micellar lipid particles suspended in an aqueous medium. The particles contain 1–25 mole percent of a PEG-derivatized lipid, and the remainder vesicle-forming lipids, in the case of liposome particles. The micellar particles contain greater than 25 mole percent of a PEG-derivatized lipid, and the remainder vesicle-forming lipids. In a preferred embodiment, the PEG-derivatized lipids are dialkyl ether-linked phospholipids, as described above.

Also included in the invention is a method of improving the oxidative stability of component lipids in a topical liposome composition, by incorporating into the liposomes about 1–10 mole percent, based on total lipid molecules, of a dialkyl ether-linked PEG-derivatized phospholipid, as described above. The PEG chain has a molecular weight of at least 2,000 daltons, and preferably between at least 10,000. In one embodiment, the molecular weight of the PEG chain is between about 2,000 and 125,000 daltons.

These and other objects and features of the invention will become more fully apparent when the following detailed

DETAILED DESCRIPTION OF THE INVENTION

I. Definitions

Figure 1:
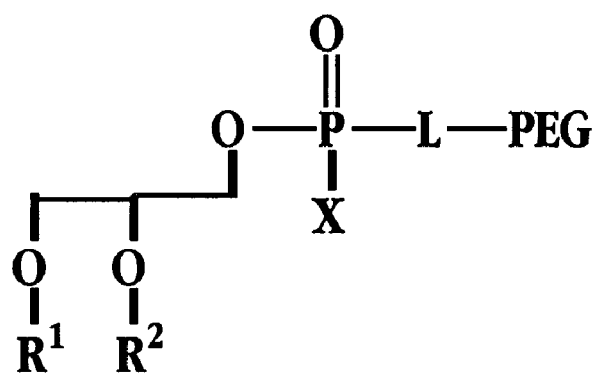
FIG. 1 shows the general structure of a dialkyl ether-linked phospholipid of the invention.

Unless otherwise indicated, the terms below have the following meaning:

A "dialkyl ether-linked phospholipid" (or ether-linked phospholipid) is a phospholipid in which the hydrocarbon chains are linked to a glyceryl moiety via an ether linkage.

A "PEG-derivatized phospholipid" (or PEG phospholipid) is a phospholipid, such as phosphatidyl choline, phosphatidyl ethanolamine, phosphatidic acid, phosphatidyl inositol, or sphingomyelin, whose head group is linked to a polyethylene glycol (PEG) chain. The hydrocarbon chains of the lipid may be attached via ether or ester linkages to a glyceryl backbone, or via an amide bond to a 2-amino-1,3-propanediol backbone.

A "dialkyl chain lipid" is a lipid containing two hydrocarbon chains, each containing ten or more carbon atoms, attached to a glyceryl or 2-amino-1,3-propanediol backbone.

A "PEG-derivatized lipid" (or PEG lipid) includes, in addition to PEG-derivatized phospholipids, other PEG-derivatized dialkyl chain lipids, as defined above. These other lipids include sphingolipids and glycolipids which are derivatized with PEG via the head group or the C-1 hydroxyl.

"Vesicle-forming lipids" refers to amphipathic lipids which have hydrophobic and polar head group moieties, and which (a) can form spontaneously into bilayer vesicles in water, as exemplified by phospholipids, or (b) are stably incorporated into lipid bilayers, with the hydrophobic moiety in contact with the interior, hydrophobic region of the bilayer membrane, and the polar head group moiety oriented toward the exterior, polar surface of the membrane.

The vesicle-forming lipids of this type typically include one or two hydrophobic acyl hydrocarbon chains or a steroid group and may contain a chemically reactive group, such as an amine, acid, ester, aldehyde or alcohol, at the polar head group. Included in this class are the phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14–22 carbon atoms in length, and have varying degrees of unsaturation. Other vesicle-forming lipids include glycolipids, such as cerebrosides and gangliosides, and sterols, such as cholesterol.

"Alkyl" refers to a fully saturated monovalent radical containing carbon and hydrogen, and which may be branched or a straight chain.

"Alkenyl" refers to monovalent radical containing carbon and hydrogen, which may be branched or a straight chain, and which contains one or more double bonds.

"Lower alkyl" refers to an alkyl group having from one to six carbon atoms, and preferably one or two carbon atoms.

II. Preparation of PEG-Derivatized Phospholipids

This section describes methods of preparation of PEG-derivatized lipids which may be used in accordance with the invention. Subsequent sections will describe the use of an ether-linked PEG phospholipid for oxidative protection of lipids in a lipid bilayer, and use of the PEG-lipids in cosmetic preparations.

FIG. 1 shows the general structure of a dialkyl ether-linked PEG-derivatized phospholipid of the invention, where $R^1$ and $R^2$ are hydrocarbon chains containing at least ten carbon atoms, and PEG is a polyethylene glycol chain having a molecular weight of at least 2,000, and preferably at least 10,000 daltons. In a preferred embodiment, the molecular weight of the PEG group is between about 2,000 and 125,000 daltons.

Figure 2A:
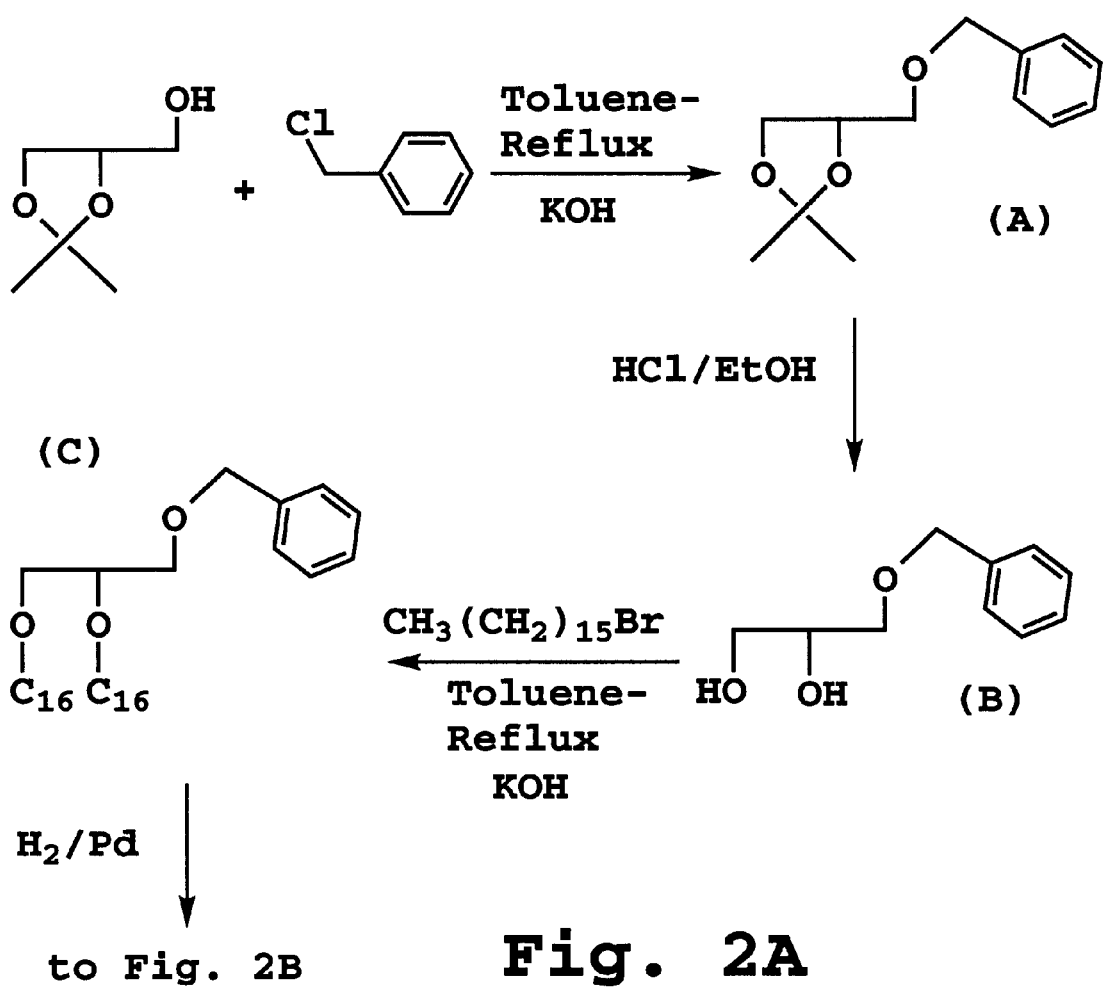
FIGS. 2A–B illustrate a reaction scheme for preparing dihexadecyl phosphatidyl polyethyleneglycol (DHP-PEG$^{2000}$), and related compounds with neutral and positively charged head groups.
Figure 2B:
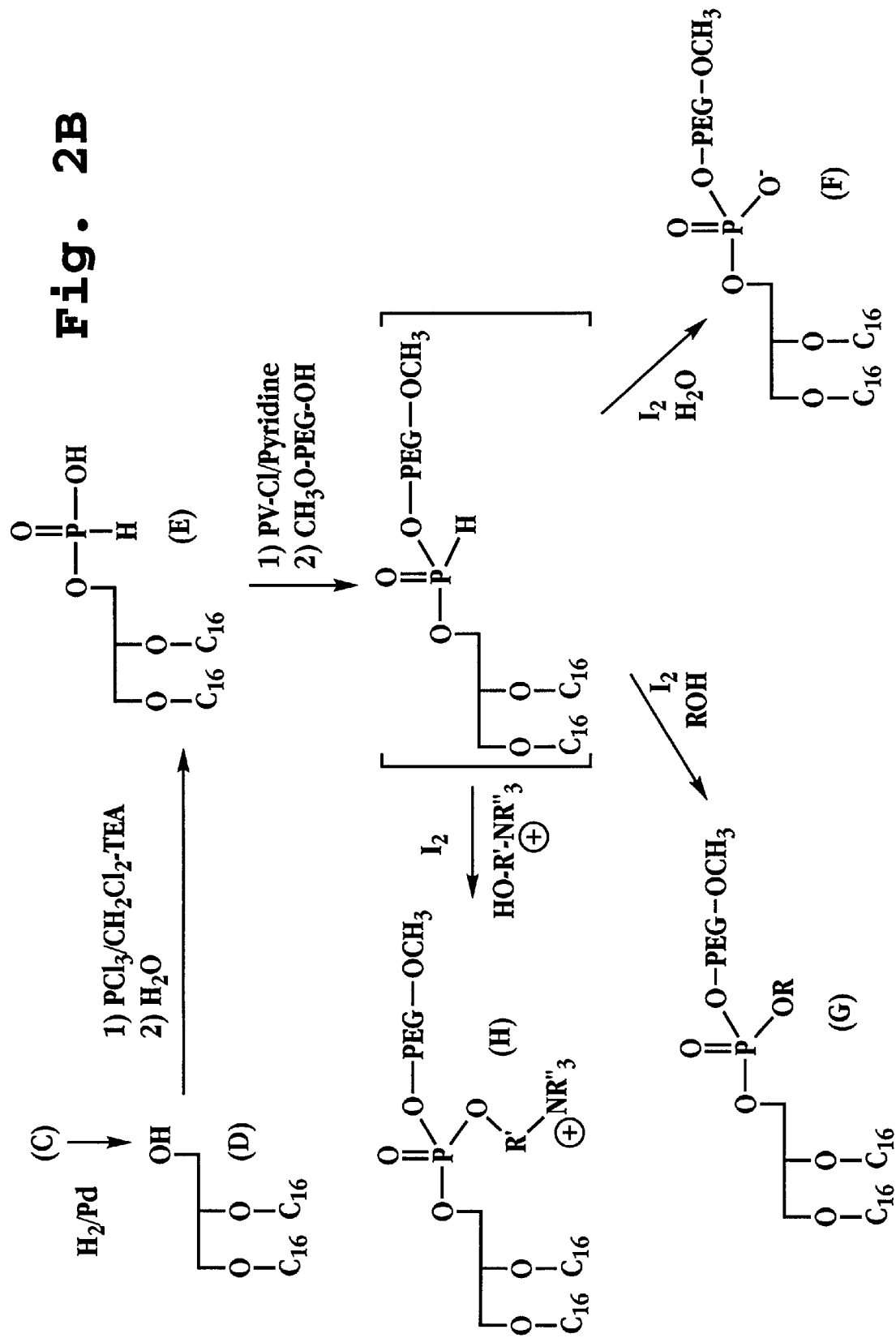

The head group of the phospholipid can have an overall negative, neutral, or positive charge. Negatively charged head groups include phosphate, where X in FIG. 1 is —O⁻; e.g. compound (F) in FIG. 2B. Formation of a phosphate ester (X=alkoxy), such as compound (G) in FIG. 2B, gives a neutral head group. Positively charged head groups include a phosphate ester whose alkyl component is substituted with an amine which is positively charged (X=amino- or ammonium-alkoxy), such as compound (H) in FIG. 2B. The linker group L, which connects the polar head group of the phospholipid to the PEG chain, may be a direct covalent bond, in which case the PEG chain is linked directly to the phosphatidic acid head group. Various other linkages are possible; for example, lipids containing a phosphatidyl ethanolamine (PE) or other amino head group may be conveniently coupled to activated PEG chains via reaction with brominated PEG. Woodle et al. (1991) describes other methods of coupling a lipid amine (specifically PE) with PEG, including activation of hydroxy-terminated PEG with a carbonyl diimidazole coupling reagent, followed by reaction with the lipid amine to form a carbamate linkage. PEG end-capped with a carboxyl group may be reacted with a lipid amine to form an amide linkage (Sears).

Differently charged head groups may be produced; e.g., alkylation of a tertiary amine-substituted lipid with PEG will provide a positively charged quaternary amine. Derivatives of phosphatidyl choline may be substituted with PEG at the phosphate oxygen to give lipids with an overall positive charge, similar to compound (H) as shown in FIG. 2B.

Lipids containing hydroxyl functionality may also be reacted with brominated PEG to form ether linkages. Parent lipids in this case include phosphatidyl glycerol and phosphatidyl inositol, as well as sphingolipids such as ceramide, glycolipids, and sterols. Phosphatidyl glycerol may also be oxidized with periodate and then reacted with amino-PEG to form an imine, which is then reduced to the stable amine adduct.

The synthetic scheme of FIG. 2 (Lindh et al., Kates et al.) shows the preparation of an ether-linked lipid with a phosphate head group, dihexadecyl phosphatidyl polyethyleneglycol (DHP-PEG$^{2000}$), and related compounds. As shown in FIG. 2, 3-O-Benzyl solketal (A) was prepared from solketal by reaction with benzyl chloride and then deprotected to give 3-O-benzyl glycerol (B). The glyceryl hydroxyls were alkylated with 1-bromohexadecane, followed by hydrogenation, to give compound (D), 1,2-di-O-hexadecyl glycerol. This compound was phosphorylated to compound (E), followed by condensation with PEG monomethyl ether and oxidation of the H-phosphate to give 1,2-Di-O-hexadecyl-sn-glycero-3-phospho-PEG$^{2000}$, sodium salt (compound F). Alternatively, oxidation with $I_2$/ROH/pyridine gave the neutral phosphate ester (compound G), and oxidation with $I_2$/HO—R'—NR"$_3^+$/pyridine gave the positively charged ammonium alkyl phosphate ester, compound H. Experimental details are provided in Example 1, below.

Compound (E) may be modified prior to derivitization with PEG to produce diether-linked analogs of other amines, e.g. phosphatidyl ethanolamine, phosphatidyl choline, etc., as discussed above, according to the method of Lindh et al. Although PEG end-capped with a methyl ether is used in the above preparation, it will be appreciated that other end groups, such as hydroxyl or carboxyl, may also be used. It will further be appreciated that a variety of lipids and linking groups, in addition to those described, are suitable for use in preparing PEG-derivatized lipids for use in the compositions of the invention.

II. Protection of the Lipid Bilayer in Liposomes Containing DHP-PEG$^{2000}$

In accordance with one aspect of the invention, a relatively low mole fraction of DHP-PEG$^{2000}$ in a lipid bilayer, e.g. a liposome, is sufficient to form a barrier of bound water which slows down diffusion of oxidizing species into the bilayer, thereby reducing susceptibility to oxidative damage, as described below and in the Examples. The ether linkages of the compounds provide additional hydrolytic stability in the presence of this water layer.

Figure 3:
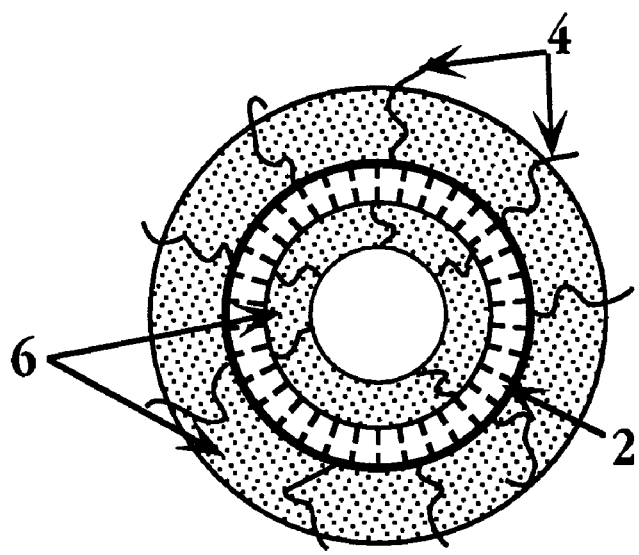
FIG. 3 is a schematic drawing of a PEG-lipid containing liposome, showing the lipid bilayer, the extended PEG chains and the hydration layer.

The presence of bound water was demonstrated by DSC studies, which indicated that each molecule of DHP-PEG$^{2000}$ binds approximately 20 times the amount of water as does a molecule of dimyristoyl phosphatidylcholine, which has an underivatized choline head group (Example 2 below). FIG. 3 is a schematic drawing of a liposome containing PEG-lipids, showing the lipid bilayer 2, the extended PEG chains 4, and the hydration layer 6.

Compounds having lower molecular weight PEG chains would be expected to absorb correspondingly less water and thus provide less protection against oxidation. It was, in fact, observed that the amount of bound water was proportionately lower (less than one third) for phospholipids having lower molecular weight (less than 750) PEG substituents, as compared to the PEG$^{2000}$ compounds described above. Additional experiments with phospholipids having higher molecular weight PEG substituents (e.g. 125,000 Da) suggested that these compounds provide equally effective protection at lower concentrations.

Oxidative stress tests were performed on egg PC liposomes containing 3 mole % of DHP-PEG$^{2000}$, using two sources of oxidizing species: (i) ionizing γ radiation and (ii) long-term exposure to air and/or high temperature. Liposomes containing egg PC alone were subjected to the same conditions. As described in Examples 3–6 below, the liposomes containing the ether-linked PEG phospholipid showed a greatly reduced loss of unsaturated acyl chains in the egg PC, compared to that in liposomes of egg PC alone.

III. Preparation of Liposomal or Micellar Suspensions Containing PEG Lipids

For use in cosmetic compositions, the PEG lipids may be formulated as liposomes, as micellar suspensions of varying consistencies, or in emulsions or microemulsions. The proportion of PEG lipid in the total lipid component may vary from 0.5 mol % to 100%, with the remainder preferably comprising vesicle-forming lipids, as discussed below. Formation of liposomes is most favorable at levels up to 25 mol % PEG-lipid. At levels of 25 mol % or greater of PEG-lipid, formation of micelles is favored.

Vesicle-forming lipids, as defined above, include phospholipids, such as phosphatidyl choline (PC), phosphatidyl ethanolamine (PE), phosphatidic acid (PA), phosphatidyl inositol (PI), and sphingomyelin (SM). Other lipids that can be included in the invention are glycolipids, such as cerebrosides and gangliosides, and sterols, such as cholesterol. The use of naturally occurring lipid mixtures such as soy lecithin or egg lecithin is described in several of the Examples below.

The following sections describe methods of preparing liposomal and micellar suspensions in accordance with the invention, and methods of incorporating additional components into these compositions.

A. Liposomes

Liposomes may be prepared by a variety of techniques, such as those detailed in Szoka et al. To form multilamellar vesicles (MLV's), a mixture of liposome-forming lipids dissolved in a suitable solvent is evaporated in a vessel to form a thin film, which is then covered by an aqueous medium. The lipid film hydrates to form MLV's, typically with sizes between about 0.1 to 10 microns. The MLV's may then be sized down to a desired size range of 1.0 microns or less by extruding an aqueous suspension of the liposomes through a polycarbonate membrane having a selected uniform pore size, typically 0.05, 0.08, 0.1, 0.2, 0.4, 0.6 or 1.0 microns. The pore size of the membrane corresponds roughly to the largest sizes of liposomes produced by extrusion through that membrane, particularly where the preparation is extruded two or more times through the same membrane.

Liposomes which encapsulate other agents, such as drugs or cosmetic components, may be prepared by the reverse phase evaporation method described by Szoka et al. in U.S. Pat. No. 4,235,871. In this method, a solution of liposome-forming lipids is mixed with a smaller volume of an aqueous medium, and the mixture is dispersed to form a water-in-oil emulsion, preferably using pyrogen-free components. Any cosmetic or pharmaceutical agent to be incorporated is added either to the lipid solution, in the case of a lipophilic agent, or to the aqueous medium, in the case of a water-soluble agent. After removal of the lipid solvent, the resulting gel is converted to liposomes. These reverse phase evaporation vesicles (REVs) have typical average sizes between about 2–4 microns and are predominantly oligolamellar, that is, containing one or a few lipid bilayer shells. The REVs may be readily sized, as discussed above, by extrusion to give oligolamellar vesicles having a maximum selected size preferably between about 0.05 to 1.0 microns.

The REV or MLV preparations can be treated, e.g. by extrusion, sonication or homogenization, to produce small unilamellar vesicles (SUV's), which are characterized by sizes in the 0.04–0.08 micron range. Alternatively, SUV's may be formed directly by homogenization of an aqueous dispersion of lipids, such as in Examples 7 and 9 below.

Liposome compositions containing an entrapped agent may be treated after final sizing, if necessary, to remove free (non-entrapped) agent. Conventional separation techniques, such as centrifugation, diafiltration, and molecular-sieve chromatography are suitable for this purpose. The composition may also be sterilized by filtration through a conventional 0.45 micron depth filter.

High viscosity in topical preparations is often desired in order to give persistence at the site of application. High viscosity liposome preparations may be formed by concentrating dilute liposome preparations, by adding thickeners such as carboxymethyl cellulose, etc., or by suspending liposomes in gel-forming colloidal materials, such as Hydrogel™, collagen, synthetic polymers, and the like, as in Examples 11 and 14 below.

A method of forming a gel-like liposome composition at relatively low lipid concentrations is described by Uster et al. Lipid concentrations preferably less than 200 mM, and more preferably 50–150 mM, can be used. The weight percent of lipid will depend on molecular weights and percentage of PEG-lipid used. For example, 50–150 mM corresponds to approximately 3.5 to 10 wt % of PE, or approximately 4 to 12 wt % of a 4:1 mole/mole mixture of PE and PE-PEG$^{2000}$.

The method involves hydration of vesicle-forming lipids having a given composition with a low-conductivity aqueous medium. The composition comprises a combination of about 50–95 weight percent neutral vesicle-forming lipids, and about 5–50 weight percent charged vesicle-forming lipids, which impart a net negative or net positive charge to the liposome surfaces. Negatively charged phospholipids include phosphatidyl glycerol, phosphatidyl inositol, and phosphatidyl serine. Examples of neutral lipids are phosphatidyl choline, sphingomyelin, glycolipids such as cerebrosides and gangliosides, and sterols such as cholesterol.

The lipids may be added directly to the low-conductivity medium, such that when the selected final lipid concentration is reached, the suspension assumes a gel-like state at room temperature. Alternatively, the lipids may be added to an aqueous medium containing about 20 mM of a zwitterionic compound, at a pH which is substantially different from the isoelectric point of the compound. In this case, the liposome suspension formed is relatively fluid and thus may be easily processed, e.g., downsized or sterilized. After processing, the non-viscous liposome suspension is converted to the desired gel form by titrating the pH of the suspension to a isoelectric point of the zwitterionic species.

B. Micelles

Micellar suspensions of PEG-lipids may be formed simply by dispersing the lipids in distilled water, or in a buffer or other aqueous solution. As noted above, inclusion of greater than 25 mole % PEG-lipids in a lipid mixture favors the formation of micelles over formation of liposomes. Viscosity may be increased as desired by concentrating or by adding thickeners or gel-forming colloidal materials, as noted for liposomes, above, and as shown in the Examples below.

IV. Formulation of Cosmetic Compositions

The dialkyl ether-linked phospholipids of the invention are useful in cosmetic formulations, where the bound water of hydration of the PEG chains imparts moisturizing, hydrating and radiation-protective properties, as described in Section II above. The compounds also possess the advantages of high hydrolytic stability, due to the alkyl ether linkages, and high lipophilicity, imparted by the two fatty alkyl chains. Useful applications include topical moisturizers which also provide protection against radiation damage, or hydration agents, e.g. in eyedrops, due to high retention of bound water by the PEG chain.

For use as skin creams or moisturizers, the total concentration of lipid may be from 0.05 to 40 wt %, depending on the desired consistency, and is preferably 3 to 25 wt %. As described above, the method of Uster et al. may also be used to impart high viscosity at relatively low lipid concentrations.

Preferably, additional components are incorporated into the liposomal or micellar suspensions of the invention in formulating the cosmetic compositions. For use as a moisturizing and radiation-blocking preparation for the skin, a UV-blocking compound is preferably included to supplement the antioxidant protection accorded by the hydrated PEG lipids. UV-blocking agents commonly used in sunscreening compositions include esters of p-methoxycinnamic acid and p-dimethylaminobenzoic acid, benzotriazoles, hydroxybenzophenones, vitamin E, betacarotene, and pigments such as titanium dioxide. Other components may be included which have properties favorable to the human epidermis, such as properties of cellular regeneration, or demulcent, emollient, cleansing, soothing, etc., properties. Examples are essential fatty acids, vegetable oils, animal oils such as squalane, glycosaminoglycans such as hyaluronic acid, and proteins such as collagen, elastin, etc. Thickening agents such as carboxymethyl cellulose, polyvinyl pyrrolidone (PVP), or Veegum K may also be added to obtain the desired viscosity, as noted above.

For use as a hydrating agent in eyedrops, the ether-linked PEG lipids of the invention are preferably included in a formulation at concentrations ranging from 0.1 to 40 wt %, and preferably 3 to 15 wt %. To prepare eye drops that are isotonic with lachrymal fluid, isotonicating agents such as sodium chloride, potassium chloride, and glycerin may be added as necessary. Other additives that may be used in formulating eyedrops include preservatives, buffering agents, viscosity-increasing agents, solubilizing agents, and stabilizers. The pH of the formulation may be at any point within an ophthalmologically acceptable range and is preferably between pH 5.0 and pH 8.0. Such formulations are well known in the art and are described, for example, in Nishida et al. and Miyazaki et al.

Preservatives or antiseptics are often used for protecting cosmetic formulations against, in particular, microbial attack, and include parabens, such as methyl para-hydroxybenzoate (methyl paraben) and propyl paraben, imidazolidinylurea, etc. Other representative active pharmaceutical substances commonly included in such formulations include vitamins, hormones, enzymes such as superoxide dismutase, vaccines, anti-inflammatory agents such as hydrocortisone, antibiotics, and bactericides.

Various methods, such as those discussed in Section III, may be used for adding additional components to liposomal or micellar compositions. Such components may be added to liposomes by the reverse phase evaporation method described above, as in Example 8, or added to an aqueous dispersion of lipids prior to homogenization to form SUV's, as in Example 9.

Aqueous liposome dispersions may also be colyophilized with other components and the resulting solid redispersed to form MLV's, which may then be downsized by extrusion or homogenization, as described in Example 14. This technique may also be applied to micellar dispersions, as in Example 15.

Thickeners or other components may generally be added directly to a micellar dispersion, as in Example 12. Alternatively, lipids may be codissolved with the desired components in an alcoholic solution which is then injected into stirred water, as in Example 13 below.

EXAMPLES

Studies performed in support of the current invention indicated that, in oxidative stress tests using PEG-lipids, oxidative damage to the PEG moiety itself was negligible, and that it does not accumulate hydroperoxides. These studies are described in the Examples below. These Examples further illustrate protection of lipid bilayers against oxidative stress by incorporation of DHP PEG$^{2000}$, and formulation of PEG lipids into various cosmetic preparations which may be used for moisturization and protection against oxidative damage from radiation.

The Examples are intended to illustrate specific compositions and methods of the invention, but are in no way intended to limit the scope of the invention.

MATERIALS AND METHODS

NMR spectra were recorded on a Varian Vxr 300S Spectrometer. One percent $H_3PO_4$ in $D_2O$ was used as an external standard for $^{31}P$ spectra. TLC was carried out on Merck (Darmstadt, Germany) silica gel 60 F254 precoated plates using a solvent system composed of chloroform:methanol:water 74:25:4 as eluent. The spots were detected using molybdenum blue spray reagent (Sigma Chemical Co., St. Louis, Mo., USA) for phosphorous compounds, and iodine as general detecting agent.

All reagents for synthesis were of analytical grade or better, purchased from Aldrich Chemical Co., Milwaukee, Wis., USA.

Determination of PL acyl chain composition in oxidative stress tests (Barenholz et al., 1993): Following oxidative stress, 100 μL of 8 mM liposomes were diluted with 900 μL of water. The lipids were extracted from the aqueous phase by adding 1 ml ethanol and 1 ml of chloroform. Two phases were formed, and the organic phase was separated and the solvent removed by a stream of nitrogen followed by 2 h lyophilization (in order to remove all water). The dry lipid was redissolved in 50 μL of toluene, 10 μL of methanol and 20 μL of meth-prep Alltech (methanol esterification reagent). The mixture of lipids was analyzed by gas chromatography using Perkin Elmer 1020 Plus GC with a Silar 10C Alltech reagent chromatographic column, using a temperature gradient of 5° C./min from 140° C. to 240° C. Saturated 16:0 palmitic acid, which is unaffected by the oxidative stress, was used as the internal standard.

Example 1

Synthesis of dihexadecyl phosphatidic acid PEG$^{2000}$ (DHP PEG$^{2000}$)

Synthesis of compound (A), 3-O-benzyl solketal (FIGS. 2A–B): Solketal 10 g (0.075 mol) and 13 g of benzyl chloride (0.092 mol) were dissolved in 500 ml of toluene. Powdered KOH (100 g) was added to the reaction mixture. The mixture was refluxed with stirring for 16 hours, and the water formed was removed by means of a Dean Stark trap. After completion, 500 ml of water was added to dissolve the KOH. The toluene phase was washed three times with water, separated, dried over magnesium sulfate, and concentrated under reduced pressure. Distillation of the residue yielded 14.6 g (0.066 mol) (88%) solketal benzyl ether, b.p 89° C./0.15 mm.

Synthesis of compound (B), 3-O-benzyl glycerol (FIG. 2A): Compound (A) (10 g) was dissolved in 100 ml of ethanol and 10 ml of concentrated HCl, and the solution was refluxed for 1 h. The reaction was monitored by TLC until the isopropylidene group had been cleaved. The ethanol was evaporated, 200 ml of water were added and the mixture was dried by freezedrying.

Synthesis of compound (C), 1,2-di-O-hexadecyl-3-O-benzyl glycerol (FIG. 2A): A mixture of 3.46 g (0.019 mol) of compound (B), 24.4 g (0.08 mol) of 1-bromohexadecane, and 11.2 g of KOH was dissolved in 200 ml toluene and refluxed with stirring for 16 h, as the water formed was removed by means of a Dean Stark trap. The cooled mixture was washed three times with water, dried over magnesium sulfate and concentrated. The residue was subjected to distillation under vacuum to remove unreacted hexadecyl bromide (b.p 105° C./0.15 mm). The residual oil (9 g, 0.014 mol, 75%) was not further purified.

Synthesis of compound (D), 1,2-di-O-hexadecyl glycerol (FIG. 2B): Compound (C) (5 g) in 200 ml of warm butanol was shaken with 1 g of 10% palladium on charcoal under hydrogen pressure of 45 psi for 10 h. The mixture was then diluted with 300 ml of chloroform and filtered to remove the catalyst. The combined filtrate was concentrated under reduced pressure, and the solid residue was crystallized from 40 ml acetone to yield 4 g (0.0074 mol), 93% yield.

Synthesis of compound (E), 1,2-di-O-hexadecyl-sn-glycero3-H-phosphonate pyridinium salt (FIG. 2B): A solution of 1 g (0.0018 mol) of compound D and 1 g (0.0099 mol) of triethyl amine in 20 ml of dichloromethane was added dropwise over 20 min to a stirred solution of 1.25 g $PCl_3$ (0.00925 mol) in 100 ml dichloromethane. Stirring was continued for 30 min, and the reaction mixture was quenched by addition of water/pyridine (1:4, v/v, 100 ml). After 15 min chloroform was added (300 ml), and the organic layer was washed with water (2×100 ml), dried with sodium sulfate, and concentrated. The solid residue was crystallized from acetone to yield 1 g (1.46 nmol, 81%) of (E).

Synthesis of compound (F), 1,2-Di-O-hexadecyl-sn-glycero3-phospho-PEG DW sodium (FIG. 2B): Compound (E), 1 g (1.46 mmol) was dissolved in 50 ml dichloromethane, and 3.5 g of lyophilized polyethyleneglycol monomethyl ether (CH3 2000 PEG-OH), 0.35 g (0.0029 mol) of pivaloyl chloride (condensing reagent) and 1 ml pyridine were added. After 10 min of stirring the reaction mixture was evaporated to dryness under reduced pressure. A solution of 0.8 g $I_2$ in 15 ml 1:1 water/pyridine was added to oxidize the H-phosphonate. After 10 min, oxidation was stopped by addition of 5% (100 ml) sodium thiosulfate. The lipid was extracted from the aqueous medium with 200 ml of chloroform. The organic layer was separated from the water, dried over magnesium sulfate, filtered and evaporated under reduced pressure. The solid residue was crystallized from acetone to yield 3.5 g (1.29 mmol, 88%). $^1H$ NMR (300 Mhz, $CDCl_3$ δ 0.7–0.8 (t,6H), δ 1.2–1.4 (s,52H), δ 1.45–1.6 (m,4H), δ 2.3–2.5 (m,9H), 3.5–3.8 (s,181H). $^{31}P$ NMR single peak 2.8 ppm. Elemental analysis: C% calc. 57.17%, found 58.17%; H% calc. 9.6%, found 10.07%. TLC: $R_f$=0.7 was obtained for DHP-PEG$^{2000}$ compared with $R_f$ for PEG and DHPA of 0.75 and 0.4, respectively.

Example 2

Quantification of Bound Water in PEG, DHP-PEG$^{2000}$, and Dimyristoyl Phosphatidylcholine (DMPC)

Bound water level was evaluated (Barenholz et al., 1983) by heat flow DSC (differential scanning calorimetry), using a Mettler Thermal Analyzer model 4000. Scanning was conducted from −30° C. to 10° C. at a rate of 2° C./min. The amount of bound water to PEG$^{2000}$ and DHP-PEG$^{2000}$ was calculated from the decrease in the fusion melting heat of the saline solutions containing the analyte, compared to free water and saline:

% of bound water to PEG in saline=
[lOO($\Delta Hf_u$ saline–$\Delta Hf_u$ PEG:saline)]/$\Delta Hf_u$ water A typical scan of saline solution featured a single peak of water melting at 0° C. $\Delta Hf_u$ (ice-water fusion heat enthalpy) was calculated from the area of the peak to be 275 j/gm for the water in saline solution. Scans were performed for pure saline and for saline solution containing increasing concentrations of $PEG^{2000}$. Forty weight percent of polyethylene glycol 2000 induced almost a complete disappearance of the free water peak, indicating that water becomes tightly bound to the PEG. $\Delta Hf_u$ of the free water was calculated to be 49 j/gm.

Figure 4:
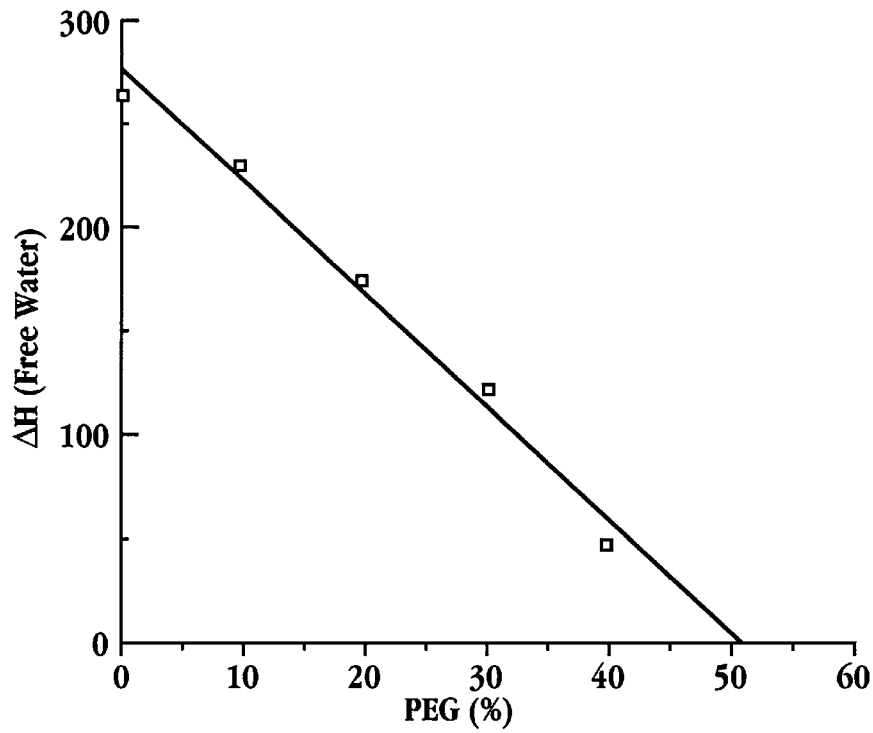
FIG. 4 shows a calibration curve of $\Delta Hf_u$ of free water vs. PEG concentration, used to determine molecules of bound water per PEG molecule.

From a calibration curve of the $\Delta Hf_u$ of free water vs. PEG concentrations (FIG. 4), it was calculated that each molecule of PEG binds 136 molecules of water. Similar studies were carried out for DHP-$PEG^{2000}$ micelles dissolved in saline at a final concentration of 10% w/w. The $\Delta Hf_u$ of the free water at this DHP-$PEG^{2000}$ concentration was found to be 210 j/gm, and the amount of bound water to each DHP-$PEG^{2000}$ molecule in the micellar solution was calculated to be 197 molecules. In comparison to DHP-$PEG^{2000}$, the $\Delta Hf_u$ value of free water of 4 mg dimyristoyl phosphatidylcholine (DMPC) in 3.2 mg of saline was 165 j/gm, with 10 molecules of bound water per molecule of lipid.

Example 3
Preparation of Liposomes for Oxidative Stress Tests

Small unilamellar liposomes were prepared from egg phosphatidylcholine (EPC 2 Lipid KG, Ludwigshafen, Germany) at 8 mM lipid concentration in 50 mL HEPES (20 mM) with saline (0.09%) buffer pH=7.2, using a Ranie 8.30 min lab. high pressure homogenizer, according to a published procedure (Haran et al.). Two preparations were made, one composed of only egg PC (egg PC SUV), and the second egg PC containing 3 mol % DHP $PEG^{2000}$ (DHP $PEG^{2000}$ SUV).

Example 4
Effect of γ Irradiation on the PEG Moiety of DHP-$PEG^{2000}$: Tests for Degradation and/or Peroxide Accumulation Liposomes containing 3 mol % of DHP-$PEG^{2000}$ were irradiated for 18 h at 1 Mrad irradiation. The lipids and the DHP-$PEG^{2000}$ were then extracted from the aqueous phase with 1 ml ethanol/1 ml of chloroform. It was expected that hydrophilic degradation products of the PEG resulting from the exposure to gamma irradiation would partition into in the aqueous phase, while the DHP-PEG was extracted with the EPC into the organic solvent. More than 95% of the phosphorus (phosphorus determination) and the $PEG^{2000}$ ($^1H$ NMR) were recovered in the chloroform rich phase, indicating that the PEG was still a part of the lipid molecule.

The chloroform phase was then dried by a stream of nitrogen for 2 h, followed by lyophilization. The dried lipids were redissolved in $CDCl_3$ and $^1H$ NMR spectra were recorded to determine the level of the PEG moiety. The $^1H$ NMR showed that damage to the DEA-$PEG^{2000}$ was minimal. Comparison between integration of peaks at 3.35 ppm (methyl head group of choline) and at 3.7 ppm (polyethyleneglycol methylene groups) before and after irradiation showed that the integration ratio changed from 1.41 to 1.40%, indicating that the loss of PEG compared to the choline group was 4.7% (standard deviation of an NMR experiment is 3%).

To determine whether the PEG accumulates peroxides, DHP-$PEG^{2000}$ (6 mol %) was incorporated into liposomes composed of phospholipids with saturated acyl chains only, using a 1:1 mixture of dimyristoyl phosphatidylcholine and dimyristoyl phosphatidylglycerol. The liposomes were irradiated at a 2.75 Mrad dose (54 h) and then assayed for peroxide accumulation according to a modified micromolar sensitive spectroscopic method (Johnson et al.): Fifty $\mu L$ of lipids was dissolved in 1 ml ethanol. Fifty $\mu L$ of 50% KI solution was added, and the mixture was incubated for 30 min in the dark. The absorbance at 400 nm was measured in a spectrophotometer. No accumulation of peroxides was found on the PEG-lipid molecules following the irradiation.

Figure 5A:
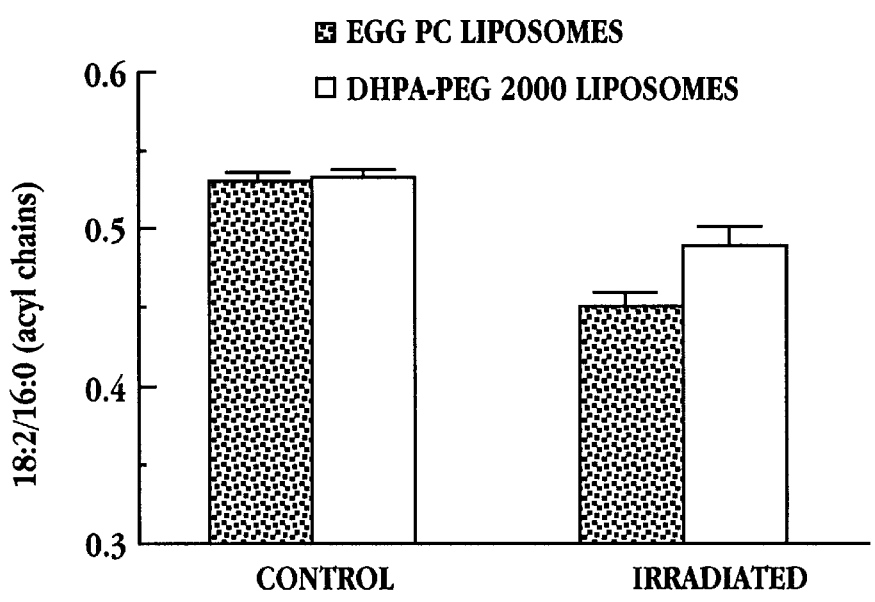
FIGS. 5A–5C show ratios of unsaturated to saturated acyl chains in egg PC liposomes vs. DHP PEG$^{2000}$/egg PC liposomes before and after gamma irradiation, for three levels of unsaturation in the egg PC acyl chains.
Figure 5B:
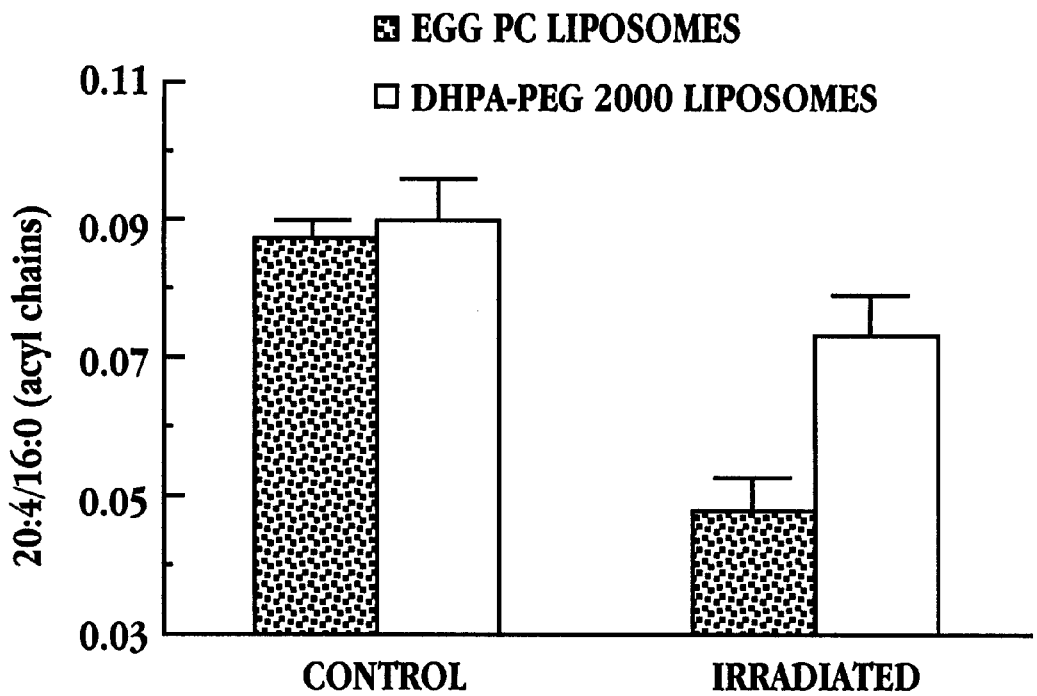
Figure 5C:
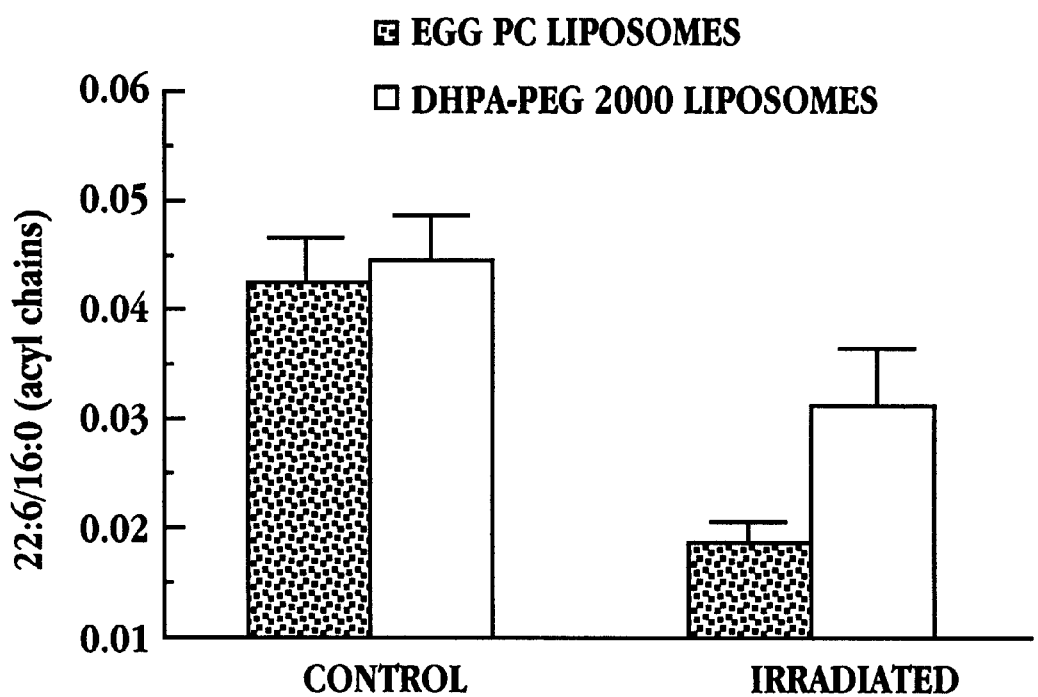

Example 5
Effect of γ Irradiation on Liposomes with and without DHP-$PEG^{2000}$ Liposomes with and without DHP-$PEG^{2000}$ were exposed to ionizing gamma radiation. The liposomes were analyzed for their acyl chain composition following the exposure as described in Materials and Methods. Three species of polyunsaturated fatty acids (PUFA) were monitored (18:2, 20:4, 22:6). FIGS. 5A–C show the ratio of unsaturated lipid to the saturated internal standard, palmitic acid (16:0), which is not affected by the irradiation. Liposome acyl chain composition prior to irradiation shows little or no difference in the fatty acid composition between the two types of liposomes, as is shown in FIGS. 5A–C in the control columns.

Ionizing irradiation at a 1 Mrad dose caused a significant loss of the PUFA in all of the liposomes; however, the loss of acyl chains in liposomes containing the DHP-$PEG^{2000}$ was significantly lower than in the liposomes composed of only egg phosphatidylcholine (FIGS. 5A–C). Each experiment was repeated six times. The average loss of 18:2, 22:4, 22:6 acyl chains in the EPC liposomes was 15%, 45% and 56% respectively, while the loss in the PEG-liposomes was 9%, 19% and 29% respectively. As expected, the loss of acyl chains increased with increasing degree of phospholipid acyl chain unsaturation for liposomes lacking and containing DHP-$PEG^{2000}$. However, the level of oxidative damage was much higher for the vesicles lacking the PEG lipid.

Figure 6A:
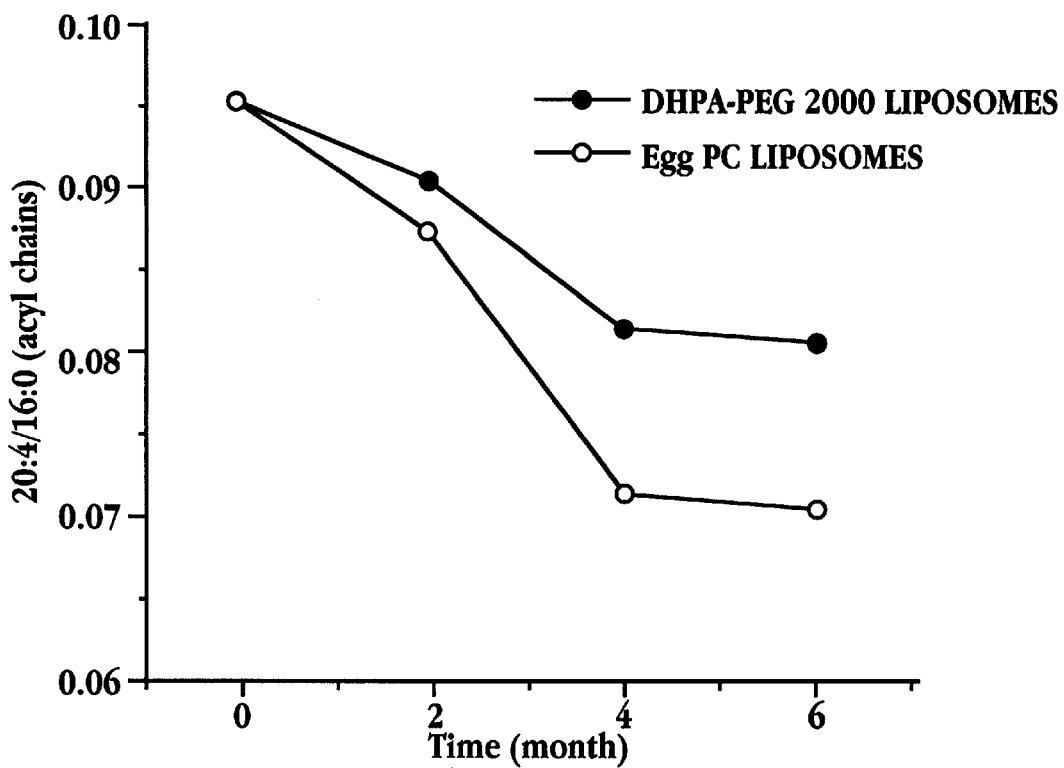
FIGS. 6A–B shows ratios of unsaturated to saturated acyl chains in egg PC liposomes vs. DHP PEG$^{2000}$/egg PC liposomes before and after extended storage at 4° C., for two levels of unsaturation in the egg PC acyl chains.
Figure 6B:
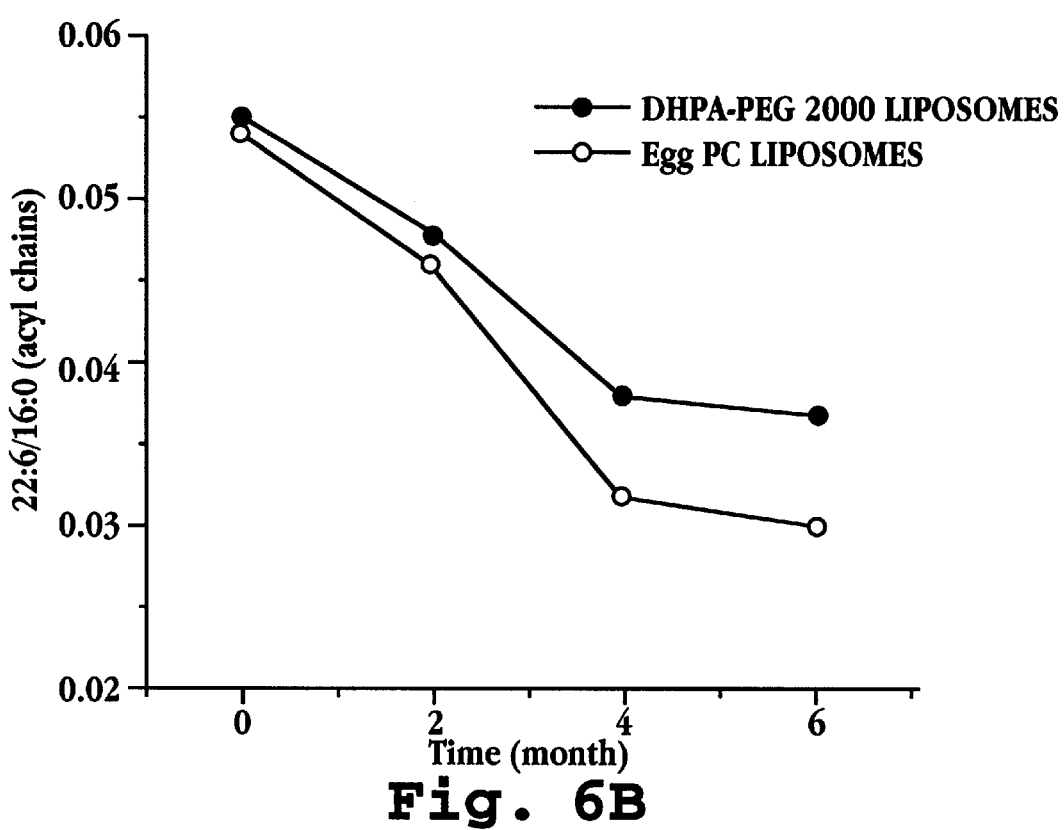

Example 6
Stability of Liposomes with and without DHP-$PEG^{2000}$ to Storage in Air Liposomes with and without DHP-$PEG^{2000}$ were incubated for a period of 6 months at 4° C. The degree of oxidation of the liposome preparation was analyzed by measuring storage time-dependent change in acyl chain composition. FIGS. 6A–B show the ratio of unsaturated lipid to the saturated internal standard, palmitic acid (16:0), which is oxidatively stable. The polyunsaturated acyl chains of the PEG liposome preparation were found to be more stable toward oxidation than in the liposomes composed of EPC only. Liposomes containing PEG, in a period of 6 months, 16% and 33% of their 20:4 and 22:6 acyl chains, respectively, compared with losses of 27% and 45%, respectively, in liposomes lacking polyethylene glycol (FIGS. 6A–B).

Figure 7:
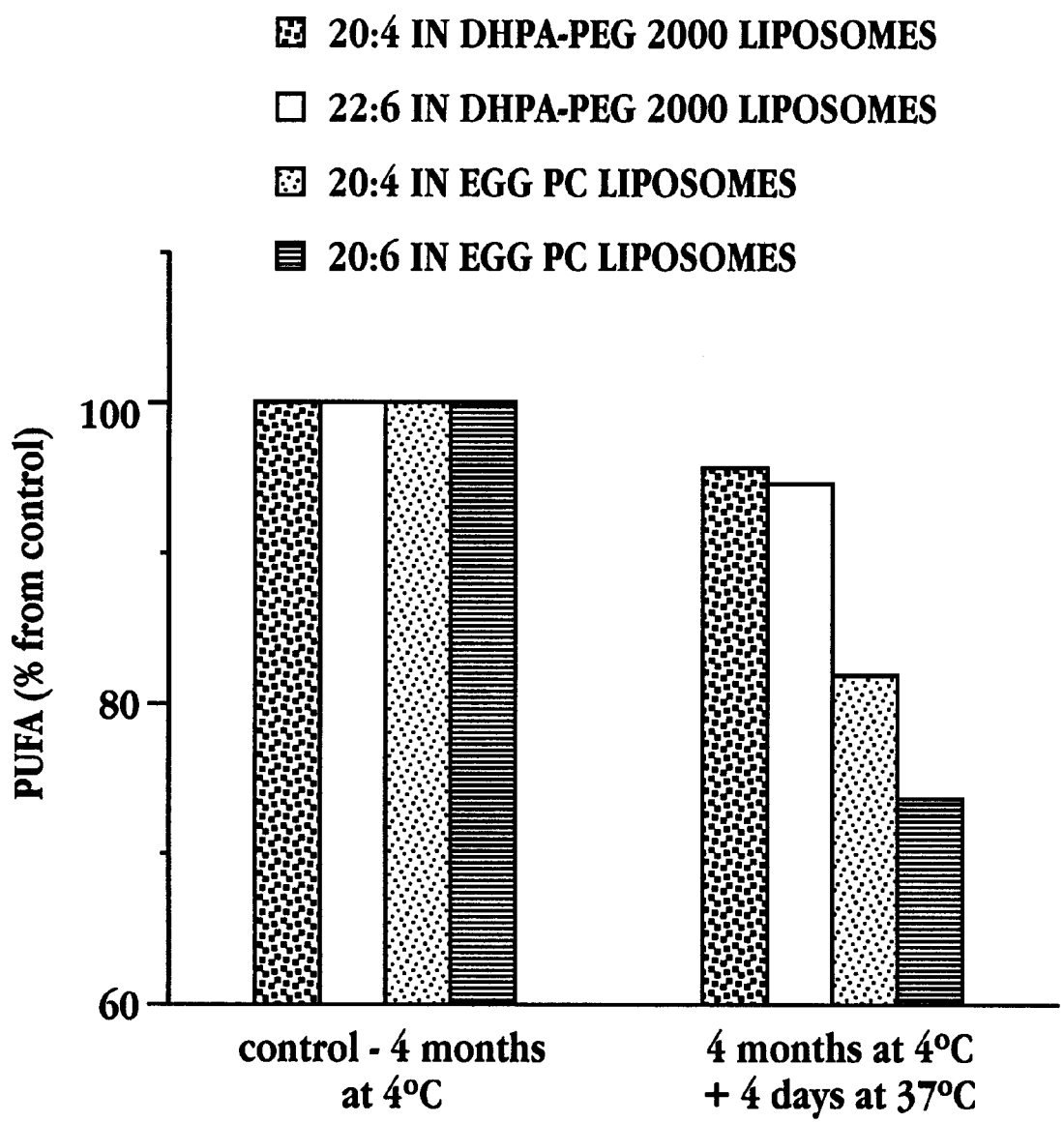
FIG. 7 shows the amount of further loss of unsaturated acyl chains in egg PC liposomes vs. DHP PEG$^{2000}$/egg PC liposomes, when liposomes stored at 4° C. are then stored for 4 days at 37° C., for two levels of unsaturation in the egg PC acyl chains.

Liposomes containing and lacking DHP-PEG2000 that had been stored for 4 months were then incubated for 4 days at 37° C., for accelerated degradation. FIG. 7 shows the amount of further loss of PUFA under this accelerated oxidation. The loss was 19% and 27% for the 20:4 and 22:6 acyl chains, respectively, for vesicles lacking DHP-$PEG^{2000}$, while the loss in the PEG liposomes was more limited (5% and 6% for the 20:4 and 22:6 fatty acids, respectively).

Example 7
Formation of SUV's Containing PEG Phospholipids

A mixture of 10 grams of soybean lecithin and 2.5 grams of PEG lipid was dispersed in 100 ml sterile distilled water, followed by 5 minutes of high pressure homogenization at 10000 psi. The liposomes formed are mostly unilamellar with sizes of <100 nm. These liposomes were used as the basis for the skin moisturizing preparations as described in Examples 13 and 14 below.

Example 8
Formation and Downsizing of Liposomes Incorporating an Antioxidant and/or UV-blocking Agent A mixture of 10 grams of egg lecithin and 2.5 grams PEG lipid containing an antioxidant, such as 0.2 mole % of vitamin E, butylated hydroxy toluene, or ascorbyl palmitate, and/or a UV-blocking agent, such as 2-ethylhexyl p-methoxycinnamate, 2-hydroxy-4methoxy-4'-methyl benzophenone, or 2-ethylhexyl p-dimethylaminobenzoate, was dissolved in 30 ml of chloroform. The solvent was removed by flash evaporation. Large multilamellar liposomes were prepared by adding 100 ml of distilled water containing a chelator, such as EDTA or DTPA, and shaking the aqueous solution with the lipid layer. Downsizing of the liposomes to a desired size was achieved by extrusion (3 times) of the multilamellar liposomes through a polycarbonate filter with pore size of I micron, 600 nm, 400 nm, 200 nm, 100 nm, and 50 nm. The pressure was adopted to the filter pore size. The differently sized liposomes were used in moisturizing formulations described in Examples 13 and 14 below.

Example 9
Formation and Downsizing of Liposomes Incorporating a Preservative A mixture of 100 g of soybean lecithin and 25 g of PEG phospholipid was dispersed in 1.0 liter of distilled water. A preservative such as bronopol, paraben or germall, or a mixture of preservatives, at bacteriostatic concentration, was added. Liposome downsizing was performed using high pressure homogenization, as described in Example 7, to give liposomes having an average size <100 nm. Optionally, gums such as sodium alginate, Acacia, or Chondrus were added to the liposomal dispersion.

Example 10
Formation of a Micellar Dispersion

Five grams of PEG-lipid were dispersed in distilled water to give a micellar dispersion as a basis for a moisturizing hydrogel or cream.

Example 11
Formation of a Liposomal Hydrogel

A thickening agent such as carboxymethyl cellulose, polyvinyl pyrrolidone (PVP), or Veegum K was added to the liposomal dispersion prepared in Example 9 to obtain the desirable viscosity. The liposomal hydrogel is used for moisturizing skin on the face and body.

Example 12
Formation of a Micellar Hydrogel

A thickening agent such as carboxymethyl cellulose, polyvinyl pyrrolidone (PVP), or Veegum K was added to the micellar dispersion prepared in Example 9 to obtain the desirable viscosity. The micellar hydrogel is used for moisturizing skin on the face and body.

Example 13
Preparation of Liposomal Moisturizing Hydrogel for Facial or Body Use The mixture of lipids used in Example 7 was dissolved in 50 ml of ethanol together with an antioxidant (Example 8), a preservative (Example 9), and a plant extract such as rose extract for cleaning and tonic, camphor extract for skin stimulation and comfort, chamomile extract for soothing, or a herbal extract. The ethanolic solution was injected at a rate of O.1 ml/min into 1 liter of stirred bidistilled water. The liposomes formed (average size <100 nm) was were used in a hydrogel as described in example 12. This preparation is used to moisturize the face and other body parts.

Example 14
Formation of a Liposomal Dispersion Incorporating Collagen/Elastin, for Use as a Skin Lotion 100 ml small unilamellar liposomes (size <50 nm) at 10 wt % soybean lipid/2.5 wt % PEG lipid were prepared in sterile bidistilled water. These liposomes were colyophilized with a 100 ml solution containing a mixture of collagen and elastin at a protein concentration in the range of 0.05 to 2.0%. The dry powder was dispersed in a final volume of 100 ml water or buffer at the desired pH. The multilamellar liposomes formed were down sized either by high pressure homogenization as described in Example 7 or by serial extrusion as described in Example 8. These liposomal moisturizers are used to replace skin lotions.

Example 15
Formation of a Micellar Dispersion Incorporating Collagen/Elastin, for Use as a Skin Lotion 100 ml micellar dispersion was prepared in sterile bidistilled water, as in Example 10 above. This micellar dispersion was colyophilized with a 100 ml solution containing a mixture of collagen and elastin at a protein concentration in the range of 0.05 to 2.0%. The dry powder was dispersed in a final volume of 100 ml water or buffer at the desired pH. The moisturizing hydrogel was used to replace skin lotions.

It is claimed:

1. A dialkyl ether-linked phospholipid having a phosphorus containing polar head group, as shown in formula I:

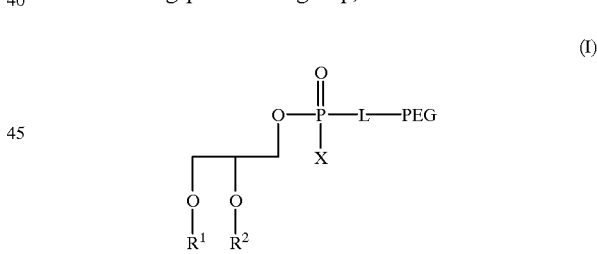

wherein $R^1$ and $R^2$ are hydrocarbon chains contaning at least ten carbon atoms, PEG represents a polyethylene glycol (PEG) chain which has a molecular weight of at least 2,000 daltons, X is —O⁻, alkoxy, aminoalkoxy, or ammonium alkoxy, and L is a linker group connecting the polar head group of the phospholipid to the PEG chain.

2. The phospholipid of claim 1, wherein the PEG chain has a molecular weight of at least 10,000 daltons.

3. The phospholipid of claim 1, wherein the PEG chain has a molecular weight between about 2,000 and 125,000 daltons.

4. The phospholipid of claim 1, which has ether-linked $C_{16}$ to $C_{24}$ alkyl or alkenyl chains.

5. The phospholipid of claim 1, wherein the polar head group has a neutral charge.

6. The phospholipid of claim 5, wherein the polar head group includes a lower alkyl phosphate ester.

7. The phospholipid of claim 1, wherein the polar head group has a negative charge.

8. The phospholipid of claim 7, wherein the polar head group includes a phosphate group.

9. The phospholipid of claim 1, wherein the polar head group has a positive charge.

10. The phospholipid of claim 9, wherein the polar head group includes a lower alkyl phosphate ester, having a lower alkyl substituent which terminates at a positively charged amine.

* * * * *